United States Patent
Rudolf et al.

(10) Patent No.: US 12,365,760 B2
(45) Date of Patent: Jul. 22, 2025

(54) PROCESS FOR THE SYNTHESIS OF POLYCARBONATES FROM CYCLIC MONOTHIOCARBONATES

(71) Applicant: BASF SE, Ludwigshafen am Rhein (DE)

(72) Inventors: Peter Rudolf, Ludwigshafen (DE); Indre Thiel, Ludwigshafen (DE); Thomas Maximilian Wurm, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 925 days.

(21) Appl. No.: 17/595,140

(22) PCT Filed: May 11, 2020

(86) PCT No.: PCT/EP2020/063015
§ 371 (c)(1),
(2) Date: Nov. 10, 2021

(87) PCT Pub. No.: WO2020/229393
PCT Pub. Date: Nov. 19, 2020

(65) Prior Publication Data
US 2022/0220254 A1    Jul. 14, 2022

(30) Foreign Application Priority Data

May 13, 2019 (EP) .................... 19174006

(51) Int. Cl.
*C08G 64/30* (2006.01)
*C08G 64/02* (2006.01)

(52) U.S. Cl.
CPC ....... *C08G 64/305* (2013.01); *C08G 64/0241* (2013.01); *C08G 64/025* (2013.01)

(58) Field of Classification Search
None
See application file for complete search history.

(56) References Cited

U.S. PATENT DOCUMENTS

| 3,326,977 A | 6/1967 | Johnson et al. |
| 9,617,238 B2 | 4/2017 | Wölfle et al. |
| 11,780,964 B2 | 10/2023 | Rudolf et al. |
| 11,814,344 B2 | 11/2023 | Rudolf et al. |
| 11,897,861 B2 | 2/2024 | Rudolf et al. |
| 2005/0113594 A1 | 5/2005 | Van Holen |
| 2018/0258226 A1 | 9/2018 | Taden et al. |
| 2018/0312718 A1 | 11/2018 | Jadhav |
| 2021/0309805 A1 | 10/2021 | Thiel et al. |

FOREIGN PATENT DOCUMENTS

| JP | H07-126221 A | 5/1995 |
| JP | H09-194580 A | 7/1997 |
| JP | H09-302094 A | 11/1997 |
| JP | 2002-020381 A | 1/2002 |
| JP | 2005-082732 A | 3/2005 |
| JP | 4414925 B2 | 2/2010 |
| JP | 2016-508493 A | 3/2016 |
| JP | 2018-533661 A | 11/2018 |
| JP | 2019-500442 A | 1/2019 |
| JP | 2020-531624 A | 11/2020 |
| JP | 2022-517403 A | 3/2022 |
| JP | 2022-531565 A | 7/2022 |
| WO | WO-2019/034469 A1 | 2/2019 |
| WO | WO-2019/034470 A1 | 2/2019 |
| WO | WO-2019/034473 A1 | 2/2019 |

OTHER PUBLICATIONS

U.S. Appl. No. 17/270,187, filed Feb. 22, 2021, 2021/0309805, Thiel et al.
U.S. Office Action dated Sep. 28, 2023, in U.S. Appl. No. 17/270,187, 13 pages.
B. Pflugfelder, "Industrial Synthesis of α-dithiols", The Belgian Chemical Industry, vol. 19, 1967, pp. 691-693.
International Search Report for PCT Patent Application No. PCT/EP2020/063015, Issued on Aug. 11, 2020, 3 pages.
Reynolds, et al., "Mercaptoethylation. II. Preparation of 2-Mercaptoethyl Carbamates and Oligoethylene Sulfides", The Journal of Organic Chemistry, vol. 26, Issue 12, Dec. 1, 1961, pp. 5111-5115.
Soga, et al., "Ringopening polymerization of ethylene monothiocarbonate", Die Makromolekulare Chemie, vol. 176, Issue 3, Mar. 1975, pp. 807-811.
Written Opinion for PCT Patent Application No. PCT/EP2020/063015, issued on Aug. 11, 2020, 5 pages.

*Primary Examiner* — Megan McCulley
(74) *Attorney, Agent, or Firm* — Grüneberg and Myers PLLC

(57) ABSTRACT

A process can be used for the synthesis of compounds containing at least one non-cyclic carbonate group, wherein a compound A) containing at least one five-membered cyclic monothiocarbonate group is reacted with at least one hydroxy group of a compound B) or of compound A) itself.

16 Claims, No Drawings

PROCESS FOR THE SYNTHESIS OF POLYCARBONATES FROM CYCLIC MONOTHIOCARBONATES

CROSS-REFERENCE TO RELATED APPLICATIONS

This application is the National Stage entry under § 371 of International Application No. PCT/EP2020/063015, filed on May 11, 2020, and which claims the benefit of priority to European Application No. 19174006.7, filed on May 13, 2019. The content of each of these applications is hereby incorporated by reference in its entirety.

BACKGROUND OF THE INVENTION

Field of the Invention

Object of the invention is a process for the synthesis of compounds comprising at least one non-cyclic carbonate group, wherein compound A) comprising at least one five-membered cyclic monothiocarbonate group is reacted with at least one hydroxy group of a compound B) or of compound A) itself.

Description of Related Art

Compounds with carbonate groups are of interest in chemical synthesis as the carbonate group imparts certain properties. Polycarbonates, for example, have good impact and temperature resistance and desired optical properties as transparency.

Organic compounds with sulfur are of interest as barrier properties, optical properties, antistatic properties and chemical resistance are or may be improved by the content of sulfur.

There is a demand to have compounds, notably polymers, that comprise different functional groups and have combined properties caused by the presence of such groups.

In WO 2019/034470 A1 and WO 2019/034473 A1 polymers are disclosed that are obtained by reacting compounds with five-membered cyclic monothiocarbonate groups with amino compounds. The ring opening reaction results in a compound with a urethane group and a thiol group. The thiol group may be reacted with unsaturated compounds or epoxy compounds. The polymers obtained comprise urethane groups and thioether groups.

D. D. Reynolds, D. L. Fields and D. L. Johnson, Journal of Organic Chemistry, 1961, page 5111 to 5115, disclose various reactions of compounds with a five membered cyclic thiocarbonate ring system, for example, a ring-opening reaction with an amino compound or a decomposition reaction to ethylene sulfide.

It was an object of this invention to provide a method for the manufacturing of compounds notably polymers with carbonate groups and further functional groups, such as sulfur containing groups. The polymers should be obtainable by an easy and effective manufacturing process which includes moderate temperatures, the lack of condensation by products as, for example, water or alcohol. The obtained polymers should have satisfying or even improved properties. Such properties are, for example, mechanical properties, optical properties, stabilities as UV and corrosion protection. There is also an interest in polymers that have functional groups that easily undergo chemical reactions, thus allowing easy modification or crosslinking of the polymers.

SUMMARY OF THE INVENTION

In a first aspect the invention relates to a process for the synthesis of compounds comprising at least one non-cyclic carbonate group, wherein a compound A) comprising at least one five-membered cyclic monothiocarbonate group is reacted with at least one hydroxy group of a compound B) or of compound A) itself.

In a further aspect, the invention relates to polymers obtainable by a process, as defined in any aspect herein.

In a further aspect, the invention relates to the carbonate compound of formula (IIIa)

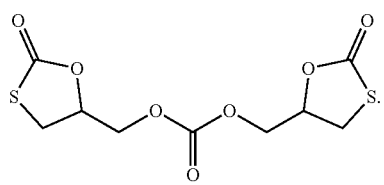 [SMILES: O=C(OCC1CSC(=O)O1)OCC1CSC(=O)O1]

DETAILED DESCRIPTION OF THE INVENTION

To Compound A)

Compound A) comprises at least one five-membered cyclic monothiocarbonate group.

The five-membered cyclic monothiocarbonate group is a ring system with 5 members, three of them are from the monothiocarbonate —O—C(═O)—S—, and the further two members are carbon atoms closing the five-membered cycle.

Compound A) may be a low molecular compound or a polymeric compound and may comprise, for example, up to 1000, notably up to 500, preferably up to 100 five-membered cyclic monothiocarbonate groups and up to 1000, notably up to 500, preferably up to 100 polymerizable, ethylenically unsaturated groups.

Compound A) may be, for example, a urethane groups comprising adduct obtained by reacting compounds with monothiocarbonate groups and compounds with primary or secondary amino groups, whereby the monothiocarbonate groups are in stoichiometric excess compared with the amino groups, thus giving a urethane groups comprising adduct which still has monothiocarbonate groups.

In a preferred embodiment, compound A) comprises one to three cyclic monothiocarbonate groups.

In a most preferred embodiment, compound A) comprises one or two five-membered cyclic monothiocarbonate groups.

Preferred compounds A) have a molecular weight of up to 10000 g/mol, notably up to 5000 g/mol and particularly up to 1000 g/mol. Most preferred are compounds A) having a molecular weight of up to 500 g/mol.

Compounds A) may comprise further functional groups, such as, for example, non-aromatic, ethylenically unsaturated groups, ether groups or carboxylic ester groups or epoxy groups or hydroxy groups.

In a preferred embodiment, compounds A) do not comprise other functional groups than cyclic monothiocarbonate groups, non-aromatic, ethylenically unsaturated groups, ether, thioether, ester or hydroxy groups.

Preferred compounds A) are compounds of formula (I)

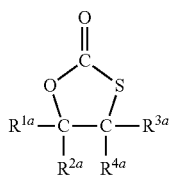

with $R^{1a}$ to $R^{4a}$ independently from each other representing hydrogen or an organic group with up to 50 carbon atoms, whereby, alternatively, $R^{2a}$, $R^{4a}$ and the two carbon atoms of the thiocarbonate group may also together form a five to ten membered carbon ring or compounds of formula (II)

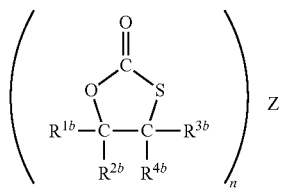

with $R^{1b}$ to $R^{4b}$ independently from each other representing hydrogen or an organic group with up to 50 carbon atoms, whereby, alternatively, $R^{2b}$, $R^{4b}$ and the two carbon atoms of the monothiocarbonate group may also together form a five to ten membered carbon ring, and with one of the groups $R^{1b}$ to $R^{4b}$ being a linking group to Z, n representing an integral number of at least 2, and Z representing a n-valent organic group.

To Compounds A) of Formula (I)

Compounds A) of formula (I) have one five-membered cyclic monothiocarbonate group, only.

In case that any of $R^{1a}$ to $R^{4a}$ represent an organic group, such organic group is preferably an organic group with up to 30, more preferably up to 20 carbon atoms. In a further preferred embodiment, $R^{2a}$ and $R^{4a}$ do not form a five to ten membered carbon ring together with the two carbon atoms of the thiocarbonate group.

In case that any of $R^{1a}$ to $R^{4a}$ represent an organic group, such organic group may comprise heteroatoms and functional groups as listed above. In particular, it may comprise oxygen, sulfur, silicon and chloride. In a preferred embodiment, the organic group may comprise oxygen or sulfur. $R^{1a}$ to $R^{4a}$ may comprise oxygen, for example, in form of ether, hydroxy, aldehyde, keto or carboxy groups. In a preferred embodiment, the organic group is an aliphatic organic group with up to 30 carbon atoms which may comprise oxygen or sulfur, in particular oxygen.

The term "chloride", as used herein, is the trivial name of a covalently bonded Cl atom. The term "halide", as used herein, is the trivial name for a covalently bonded halogen atom.

In a more preferred embodiment, the organic group is selected from an alkyl group, from a group —$CH_2$—O—$R^{5a}$ or a group —$CH_2$—O—C(=O)—$R^{6a}$ or a group —$CH_2$—$NR^{7a}R^{8a}$, with $R^{5a}$ to $R^{8a}$ being an organic group with up to 30 carbon atoms, preferably up to 20 carbon atoms. In particular, $R^{5a}$ to $R^{8a}$ represent an aliphatic or aromatic group, which may comprise oxygen, for example, in form of ether groups. In a preferred embodiment, $R^{5a}$ to $R^{8a}$ represent an aliphatic hydrocarbon group, such as an alkyl group with 1 to 10 carbon atoms, an alkoxy group or a poly-alkoxy group. In a most preferred embodiment, $R^{5a}$ to $R^{8a}$ represent an aliphatic hydrocarbon group, notably an alkyl group with 1 to 10 carbon atoms.

In a most preferred embodiment, the organic group is a group —$CH_2$—O—$R^{5a}$ or a group —$CH_2$—O—C(=O)—$R^{6a}$.

Preferably, two to all four of $R^{1a}$ to $R^{4a}$ in formula (I) represent hydrogen, and the remaining groups $R^{1a}$ to $R^{4a}$ represent an organic group.

More preferably, two and/or three of $R^{1a}$ to $R^{4a}$ in formula (I) represent hydrogen, and the remaining groups $R^{1a}$ to $R^{4a}$ represent an organic group.

Most preferably, three of $R^{1a}$ to $R^{4a}$ in formula (I) represent hydrogen, and the remaining group of $R^{1a}$ to $R^{4a}$ represents an organic group. In a preferred embodiment, $R^{1a}$ or $R^{2a}$ is the remaining group representing an organic group.

As preferred compounds A) with one five-membered monothiocarbonate group may be mentioned, for example, compounds A) of formulae:

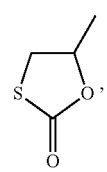 (Ia)

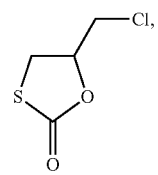 (Ib)

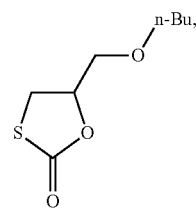 (Ic)

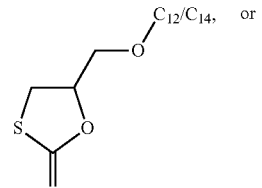 (Id)

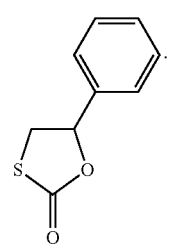 (Ie)

The substituent "$C_{12/14}$" means a substituent derived from $C_{12}/C_{14}$ fatty alcohol.

To Compounds A) of Formula (II)

Compounds A) of formula (II) have at least two five-membered cyclic monothiocarbonate groups.

In case that any of $R^{1b}$ to $R^{4b}$ represent an organic group, such organic group is preferably an organic group with up to 30 carbon atoms. In a further preferred embodiment, $R^{2b}$ and $R^{4b}$ do not form a five to ten membered carbon ring together with the two carbon atoms of the thiocarbonate group.

In case that any of $R^{1b}$ to $R^{4b}$ represent an organic group, such organic group may comprise other elements than carbon and hydrogen. In particular, it may comprise oxygen, nitrogen, sulfur and chloride. In a preferred embodiment, the organic group may comprise oxygen or chloride. $R^{1b}$ to $R^{4b}$ may comprise oxygen, for example, in form of ether, hydroxy, aldehyde, keto or carboxy groups.

One of the groups $R^{1b}$ to $R^{4b}$ is the linking group to Z.

Preferably, the linking group is simply a bond or a group $CH_2$— or $CH_2$—O— or $CH_2$—O—C(=O)— or $CH_2$—O—C(=O)—O—$CH_2$— or $CH_2$—$NR^{5b}$—, with $R^{5b}$ being an aliphatic group, notably an alkyl group with at maximum 20 carbon atoms.

More preferably, the linking group is simply a bond or a group $CH_2$— or a group $CH_2$—O— or a group $CH_2$—O—C(=O)—.

In a most preferred embodiment, the linking group is a group $CH_2$—O—.

Preferably, two or three of the groups $R^{1b}$ to $R^{4b}$ in formula (II) are hydrogen.

In a most preferred embodiment, three of the groups $R^{1b}$ to $R^{4b}$ represent hydrogen, and the remaining group of $R^{1b}$ to $R^{4b}$ is the linking group to Z.

In a most preferred embodiment, groups $R^{1b}$ or $R^{2b}$ is the linking group to Z.

n represents an integral number of at least 2. For example, n may be an integral number from 2 to 1000, specifically from 2 to 100, respectively 2 to 10.

In a preferred embodiment, n is an integral number from 2 to 5, in particular n is 2 or 3.

In a most preferred embodiment, n is 2.

Z represents a n-valent organic group. In case of a high number of n, such as, for example, 10 to 1000, Z may be a polymeric group, in particular a polymer-backbone, obtained, for example, by polymerization or copolymerization, such as radical polymerization of ethylenically unsaturated monomers, polycondensation or polyaddition. For example, polyesters or polyamides are obtained via polycondensation under elimination of water or alcohol, and polyurethanes or polyureas are obtained via polyaddition.

Such compounds of formula (II) are, for example, polymers obtained by radical polymerization or copolymerization of ethylenically unsaturated momomers comprising monothiocarbonate groups or of monomers comprising epoxy groups which are then transferred into a monothiocarbonate group.

In a preferred embodiment, Z is a n-valent organic group with up to 50 carbon atoms, in particular up to 30 carbon atoms, and which may comprise other elements than carbon and hydrogen, and n is an integral number from 2 to 5, notably 2 or 3, most preferred 2.

In a particularly preferred embodiment, Z is a n-valent organic group with up to 50 carbon atoms, in particular up to 30 carbon atoms, and which comprises carbon, hydrogen and optionally oxygen, only and no further elements, and n is an integral number from 2 to 5, notably 2 or 3, most preferred 2.

Z may be a polyalkoxylene group of formula (G1)

$$(V-O-)_m V$$

wherein V represents a $C_2$-$C_{20}$-alkylene group, and m is an integral number of at least 1. The terminal alkylene groups V are bonded to the linking group, which is one of the groups $R^{1b}$ to $R^{4b}$, see above.

Preferably, the $C_2$-$C_{20}$-alkylene group is a $C_2$-$C_4$-alkylene group, in particular ethylene or propylene. m may, for example, be an integral number from 1 to 100, in particular from 1 to 50.

Z may also be a group of formula (G2)

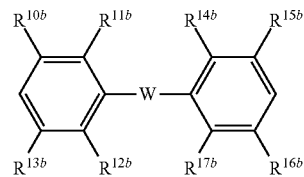

W is a bi-valent organic group with at maximum 10 carbon atoms, and n is 2, and $R^{10b}$ to $R^{17b}$ independently from each other represent H or a $C_1$-$C_4$-alkyl group and wherein the two hydrogen atoms in the para position to W are replaced by the bond to the linking group, which is one of the groups $R^{1b}$ to $R^{4b}$, see above.

Preferably, at least six of $R^{10b}$ to $R^{17b}$ are hydrogen. In a most preferred embodiment, all of $R^{10b}$ to $R^{17b}$ are hydrogen.

Groups W are, for example:

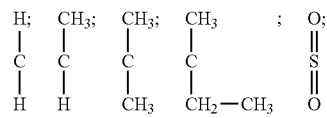

Preferably, W is an organic group that consists of carbon and hydrogen, only.

Most preferred W is

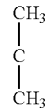

which corresponds to the structure of bisphenol A.

Z may further be a group G3, wherein G3 represents an alkylene group, notably a $C_2$-$C_8$-alkylene group; preferred examples of such an alkylene group are ethylene ($CH_2$—$CH_2$), n-propylene ($CH_2$—$CH_2$—$CH_2$) and notably n-butylene ($CH_2$—$CH_2$—$CH_2$—$CH_2$).

Particularly preferred compounds A) with at least two five-membered cyclic monothiocarbonate groups are compounds of formula (III)

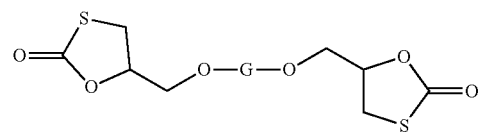

wherein G represents an organic group, for example, an alkylene group with 2 to 10, notably 2 to 6 carbon atoms or a carbonate group.

An example of a compound of formula (III) is 1,2-cyclohexanedicarboxylic acid-1,2-bis[2-oxo-1,3-oxathiolane-5-yl]ester of formula

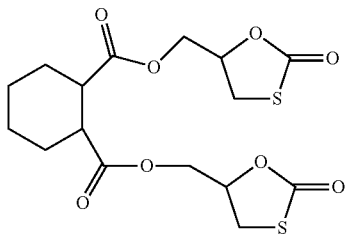 [SMILES: O=C1OC(COC(=O)C2CCCCC2C(=O)OCC2CSC(=O)O2)CS1]

A preferred compound of formula (III) is bis-1,3-oxathiolane-2-one-5,5'-[1,4-butanediylbis-(oxymethylene)] which has the formula

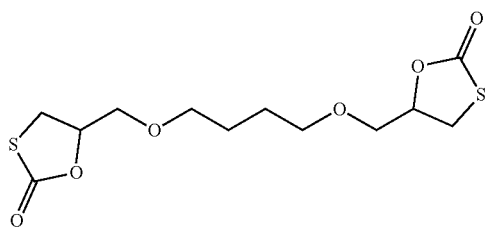 [SMILES: O=C1OC(COCCCCOCC2CSC(=O)O2)CS1]

A particularly preferred compound of formula (III) is the carbonate compound of formula (IIIa)

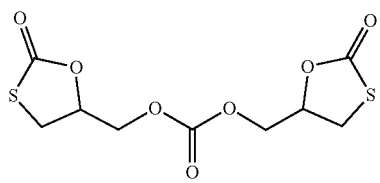 [SMILES: O=C(OCC1CSC(=O)O1)OCC1CSC(=O)O1]

To compounds A) with a polymerizable, ethylenically unsaturated group:

Compounds A) may also comprise at least one polymerizable, ethylenically unsaturated group.

Preferred compounds A) with at least one polymerizable, ethylenically unsaturated group are compounds A) of formula (I), wherein one of $R^{1a}$ to $R^{4a}$ represents an organic group comprising one polymerizable, ethylenically unsaturated group and the remaining three of $R^{1a}$ to $R^{4a}$ represent hydrogen or an organic group with at maximum 20 carbon atoms; preferably the remaining three of $R^{1a}$ to $R^{4a}$ represent hydrogen.

Preferred examples of polymerizable, ethylenically unsaturated groups are the vinyl group $H_2C=CH-$, the olefinic group $-HC=CH-$, wherein the two carbon atoms of the double bond are each substituted by one hydrogen, only, and the further substituents are notably carbon atoms, and the acrylic or methacrylic group, shortly referred to as (meth)acrylic group. In this patent application the term "vinyl group" does not include the (meth)acrylic group.

In a more preferred embodiment, the non-aromatic, ethylenically unsaturated group is a (meth)acrylic group, most preferably a methacrylic group.

Preferably, compound A comprises no or at least one non-aromatic, ethylenically unsaturated group.

In a particularly preferred embodiment, compound A comprises at least one non-aromatic, ethylenically unsaturated group, notably one non-aromatic, ethylenically unsaturated group.

Examples for compounds A) with a non-aromatic, ethylenically unsaturated group are 5-butenyl-1,3-oxathiolane-2-one of formula:

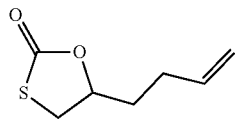

5-ethenyl-1,3-oxathiolane-2-one of formula:

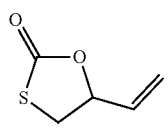

5-(ethenyloxy)methyl-1,3-oxathiolane-2-one of formula:

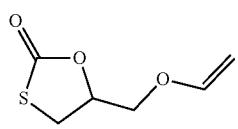

5-(2-propen-1-yloxy)methyl-1,3-oxathiolane-2-one of formula:

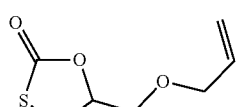

5-(methacryloyloxy)methyl-1,3-oxathiolane-2-one of formula:

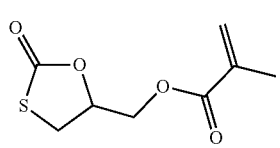

and 5-(acryloyloxy)methyl-1,3-oxathiolane-2-one of formula:

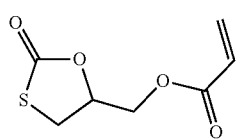

Most preferred are 5-(methacryloyloxy)methyl-1,3-oxathiolane-2-one and 5-(acryloyloxy)methyl-1,3-oxathiolane-2-one.

An example for compounds with an epoxy group is the compound of formula:

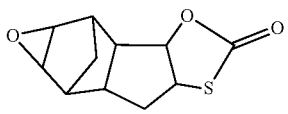

To the Synthesis of Compounds A)

Some methods for the synthesis of compounds with one monothiocarbonate group are described in the state of the art.

According to U.S. Pat. Nos. 3,072,676 and 3,201,416 ethylene monothiocarbonates may be prepared by a two-step-process. In a first step mercaptoethanol and chloro carboxylates are reacted to give hydroxyethylthiocarbonate, which is heated in the second step in the presence of a metal salt catalyst to the ethylene monothiocarbonate.

According to U.S. Pat. No. 3,517,029 alkylene monothiocarbonates are obtained by reacting mercaptoethanol and a carbonate diester in the presence of a catalytically active salt of thorium.

According to the process disclosed in U.S. Pat. No. 3,349,100 alkylene monothiocarbonates are obtained by reacting an epoxide with carbonyl sulfide. The availability of carbonyl sulfide is limited. Yields and selectivities of alkylene monothiocarbonates obtained are low.

A synthesis using phosgene as starting material is known from U.S. Pat. No. 2,828,318. Phosgene is reacted with hydroxymercaptanes. Yields of monothiocarbonates are still low, and by-products from polymerization are observed.

A preferred process for the preparation of compounds A) is a process, wherein
a) a compound with at least one epoxy groups (shortly referred to as epoxy compound) is used as starting material
b) the compound is reacted with phosgene or an alkyl chloroformate thus giving an adduct, and
c) the adduct is reacted with a compound comprising anionic sulfur to give the compound with at least one five-membered cyclic monothiocarbonate groups This process is in detail described in WO 2019/034469 A1.

To Compounds B)

Compound B) is a compound with at least one hydroxy group.

Compound B) may have, for example, a molecular weight of up to 500.000 g/mol. The latter might be the case if compound B) is a high molecular compound such as a polymer comprising hydroxy groups.

In case of a polymer the term "molecular weight", as used herein, means the number average molecular weight Mn, as usually determined by gel-permeation chromatography (GPC) against polystyrene as standard.

Preferred compounds B) have a molecular weight of up to 10000 g/mol, notably of up to 5000 g/mol and particularly of up to 1000 g/mol. Most preferred are compounds B) having a molecular weight of from 60 g/mol to 500 g/mol.

Compounds B) do not comprise any monothiocarbonate groups.

Compounds B) do not comprise primary or secondary amino groups.

Compounds B) may comprise, for example, polymerizable, ethylenically unsaturated groups, ether or carboxylic ester groups.

In a preferred embodiment, compounds B) do not comprise any other functional groups than hydroxy groups, non-aromatic, ethylenically unsaturated groups or ether groups.

In a preferred embodiment compounds B) comprise 1 to 10 hydroxy groups, preferably 1 to 5 hydroxy groups and, in a most preferred embodiment, compound B) comprises 1 to 3 hydroxy and notably 1 or 2 hydroxy groups.

Compounds B) with one hydroxy group are, for example, $C_1$-$C_{20}$-alkanols or alkenols or phenolic alcohols or tertiary amino-functionalized alcohols.

Compounds B) with at least two hydroxy groups are, for example, aliphatic or aromatic low molecular weight compounds with 1 to 5 hydroxy groups, such as alkandioles and alkantrioles as ethylene glycol, propane-1,2-diol, propane-1,3-diol, butane-1,4-diol, butene-1,4-diol, pentane-1,5-diol, neopentyl glycol, bis(hydroxymethyl)cyclohexanes such as 1,4-bis(hydroxymethyl)cyclohexane, 2-methylpropane-1,3-diol, trimethylolpropane, pentaerythrite, methylpentanediols, glycerol, isosorbide, bisphenol-A or carbohydrates.

Compounds B) may have further functional groups, such as, for example, tertiary amino groups, thiol groups, thioether groups and non-aromatic, ethylenically unsaturated groups. Such compounds are, for example, triethanolamine, allylalcohol, hydroxyethyl(meth)acrylate, vinylmercaptoethanol, glycidol or urethane alcohols.

Compounds B) with higher molecular weight are, for example, di- or polyetherpolyols, di- or polyesterpolyols or polymers obtained by (co)polymerization of ethylenically unsaturated compounds with hydroxy groups.

Preferred di- or polyesterpolyols have two to eight, preferably two to five hydroxy groups, more preferably two or three, in particular two hydroxy groups and are obtainable by reacting polyols, notably diols, with polycarboxylic acids, notably dicarboxylic acids.

Preferred di- or polyetherpolyols have two to eight hydroxy groups, preferably two to five hydroxy groups, most preferably two hydroxy groups, and are obtainable in particular by polymerizing ethylene oxide, propylene oxide, butylene oxide, tetrahydrofuran, styrene oxide or epichlorohydrin with itself, in the presence of a catalyst. Particularly preferred di- or polyetherpolyols are diethylene glycol, triethylene glycol, tetraethylene glycol, polyethylene glycol, dipropylene glycol, polypropylene glycol, and dibutylene glycol and polybutylene glycol and polytetrahydrofuran.

A preferred polymer obtained by (co)polymerization of ethylenically unsaturated compounds with hydroxy groups is, for example, a poly(meth)acrylate which consists to at least 50 mol %, more preferably at least 80 mol % of (meth)acrylic monomers, for example, of hydroxyethyl (meth)acrylate.

To Compound C)

Compounds C) comprise at least one functional group that reacts with a group —SH.

Compounds C) do not comprise cyclic monthiocarbonate groups.

Compounds C) do not comprise hydroxy groups, primary or secondary amino groups.

In a particularly preferred embodiment, compounds C) do not comprise other functional groups than functional groups selected from the functional groups which react with the group —SH, carboxylic ester groups or ether groups.

Compounds C) may have, for example, a molecular weight of up to 500.000 g/mol. The latter might be the case if compound C) is a high molecular compound such as a polymer comprising functional groups that react with a group —SH.

Preferred compounds C) have a molecular weight of up to 1000 g/mol. Most preferred are compounds C) having a molecular weight of from 60 g/mol to 500 g/mol.

Compounds C) may have, for example, up to 1000 functional groups that react with a group —SH, in particular up 500 and preferably up to 100 functional groups that react with a group —SH.

In a preferred embodiment, compound C) comprises 2 to 10 functional groups that react with a group —SH.

In a most preferred embodiment, compound C) comprises 2 or 3 functional groups that react with a group —SH.

In a preferred embodiment, the reaction of the functional group of compound C) with the group —SH results in the formation of a sulfur-carbon bond.

The reaction of the functional group of C) with the group —SH may be an addition reaction, a condensation reaction or a nucleophilic substitution reaction.

Compounds C) that undergo an addition reaction with the group —SH are, for example, compounds with non-aromatic, ethylenically unsaturated groups or compounds with epoxy groups as functional groups. Non-aromatic, ethylenically unsaturated groups may be non-aromatic carbon-carbon double bonds or carbon-carbon triple bonds.

A triple bond may react twice with —SH. In a first reaction, an —SH group may undergo an addition reaction to the triple bond, whereby the triple bond becomes a double bond. The double bond formed may react with a further group —SH. Hence one triple bond is equivalent to two functional groups that react with a group —SH.

Compounds C) that undergo a condensation reaction with the group —SH are, for example, compounds with carbonyl groups as functional group, for example, mono carbonyl compounds or dicarbonyl compounds such as dialdehydes or diketones.

Compounds C) that undergo a nucleophilic substitution reaction with the group —SH are, for example, compounds with a halide, in particular chloride, as functional group.

Preferably, the functional groups of compound C) that react with —SH are selected from polymerizable, ethylenically unsaturated groups and epoxy groups.

To Compounds C) with Non-Aromatic, Ethylenically Unsaturated Groups

Preferred examples of a non-aromatic, ethylenically unsaturated group are the vinyl group $H_2C=CH-$, the olefinic group $-HC=CH-$, wherein the two carbon atoms of the double bond are each substituted by one hydrogen, only, and the further substituents are notably carbon atoms, including carbon atoms of a cyclic system, and the acrylic or methacrylic group, shortly referred to as (meth)acrylic group. In this patent application the term "vinyl group" does not include the (meth)acrylic group. Furthermore non-aromatic, ethylenically unsaturated groups may be carbon-carbon triple bonds such as in acetylene. As such groups react twice, they correspond to two non-aromatic, ethylenically unsaturated groups.

Particularly preferred non-aromatic, ethylenically unsaturated groups for compounds C) are the vinyl group and the (meth)acrylic group.

The most preferred non-aromatic, ethylenically unsaturated group of compounds C) is the methacrylic group.

Compounds C) with one non-aromatic, ethylenically unsaturated group are, for example, (meth)acrylic acid, (meth)acrylic esters, (meth)acrylonitrile, itaconic esters or lactones, citraconic esters or lactones, vinylesters, for example, vinyl acetate, vinyl ethers, vinyl lactames, for example, N-vinyl pyrrolidone, vinyl aromatics as styrene, vinyl halogenides as vinyl chloride or vinyl fluoride or olefines with one carbon-carbon double bond, such as ethylene, propylene or cyclic olefin compounds like norbornene type compounds.

Compounds C) with more than one non-aromatic, ethylenically unsaturated groups are, for example, compounds with at least two (meth)acrylic groups, at least two vinyl groups or olefines with at least two carbon-carbon double bonds or polyolefines, such as polybutadiene or polyisoprene and unsaturated polyesters notably polyesters of maleic acid, fumaric acid, itaconic acid and/or citraconic acid.

Olefins with exactly two carbon-carbon double bonds are, for example, butadiene, cyclooctadiene, cyclododecatriene, norbornadiene, vinyl-norbornene, isoprene, limonene, divinyl cyclohexane or dicyclpentadiene, diallylether, divinylether, for example, butanediol divinylether.

Oligomers with at least two acrylic or methacrylic groups are in particular (meth)acrylic esters of polyfunctional alcohols or of alkoxylated polyfunctional alcohols or compounds obtained by reacting (meth)acrylic compounds that have hydroxy groups, for example, hydroxy alkyl (meth)acrylates, with compounds having at least one isocyanate group.

(Meth)acrylic esters of polyesterols may also be mentioned as oligomers.

Adducts of (meth)acrylic acid and epoxide compounds (known as epoxy based vinylesters) or urethane (meth) acrylates may also be suitable oligomers.

Oligomers with at least two vinyl groups are, for example, divinylether such as diethylene glycol- or triethylene glycol-divinylether.

In a preferred embodiment, compounds C) with non-aromatic ethylenically unsaturated groups are (meth)acrylic compounds, in particular (meth)acrylates of polyfunctional alcohols, or compounds with vinyl ether groups or unsaturated polyesters. In a particularly preferred embodiment compounds C) with polymerizable ethylenically unsaturated groups are methacrylic compounds.

To Compounds C) with Epoxy Groups

Compounds C) with at least one epoxy group are, for example, compounds obtained by reacting the compounds with at least one alcohol groups with epichlorohydrin.

Compounds C) with one epoxy group are, for example, epichlorohydrin or derivatives thereof, wherein the chloride of epichlorohydrin is replaced by a hydroxy group (glycidol), ether group (glycidyl ether), ester group (glycidyl ester) or amino group (glycidyl amine).

Examples of compounds C) with at least two epoxy groups which may be mentioned are the diglycidyl ethers of bisphenol A or bisphenol F or bisphenol S and the diglycidylethers of hydrogenated bisphenol A or bisphenol F or diglycidylethers of aliphatic diols such as diglycidylethers of polyalkoxylene diols. Mentioned may be also oligoglycidylether based on oligoalcohols. Examples are also epoxy resins which are obtainable by using the compounds with at least two alcohol groups in excess compared to the epichlorhydrin. In such epoxy resins the degree of polymerization of the compound with at least two alcohol groups is preferably from 2 to 25, in particular from 2 to 10. Further examples are epoxidized novolacs.

Further examples are epoxidized fatty acids, fatty acid esters or fatty acid alcohols which have at least two epoxy groups.

To the Synthesis of Compounds with at Least One Non-Cyclic Carbonate Group

Any reference to compound A) made in this patent application shall include a mixture of different compounds A), as well as any reference to compound B) shall include a mixture of different compounds B), if not otherwise stated or obvious from the context.

The five-membered, cyclic monothiocarbonate group of compound A) is opened by reaction of A) with a hydroxy group of compound B) as shown in the reaction scheme below:

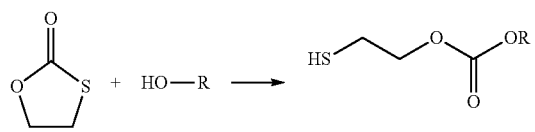

The compound obtained comprises a non-cyclic carbonate group and a thiol group.

If a compound A) with two five-membered, cyclic monothiocarbonate groups and a compound B) with two hydroxy groups are reacted, polyaddition occurs as shown below:

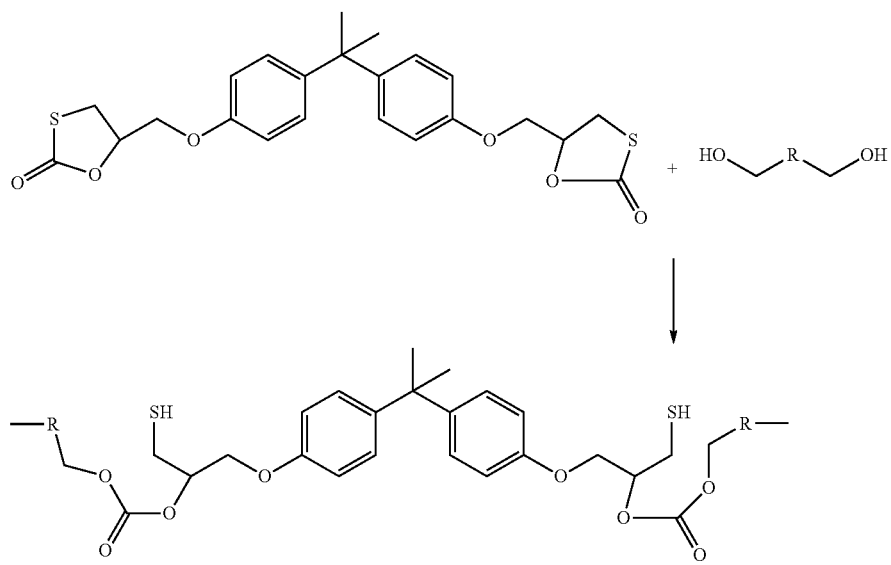

The polymer obtained has repeating carbonate groups and thiol groups.

The reaction of compounds A) and B) may be performed at temperatures of from −20 to 250° C., preferably between 20 and 100° C. and more preferably between 30 and 100° C. Alternatively, any activation energy for the reactions may be provided by high-energy radiation such as visible or UV-light. Usually, the reaction is performed at normal pressure.

The reaction may be performed with solvent. The use of a solvent might be helpful, in case that at least one of the compounds A) or B) is solid, and the other compound or compounds do not already act as solvent for the solid compounds.

Suitable solvents are, for example, methyl ethyl ketone, dioxane, water, tetrahydrofuran and dimethylformamide, chlorinated solvents and aromatic solvents.

In a preferred embodiment, the hydroxy groups of compound B) or of compound A) are transferred into the respective alcoholate groups. This may be done in a separate step before the reaction with the five-membered cyclic monothiocarbonate groups or, alternatively, by using a catalyst used in the reaction.

In a preferred embodiment, the reaction of the five-membered cyclic monothiocarbonate groups of compounds A) with the hydroxy groups of compound B) or compound A) itself is performed in the presence of a catalyst.

The catalyst is preferably a basic catalyst which transfers the hydroxy group into an alcoholate group or a catalyst capable of activating the carbonyl group of the five-membered cyclic monothiocarbonate group.

Useful catalysts are, inter alia, compounds which abstract the hydrogen of the hydroxy group and become a cation or activate the carbonyl group of the five-membered cyclic monothiocarbonate group. Such compounds are in particular compounds with a tertiary amino group, for example, Versamin®, compounds with an amidine or guanidine group or phosphines.

In a preferred embodiment, compound B) itself or compound A) itself may serve as catalyst. Suitable compounds B) with catalytic activity are notably compounds with at least one hydroxy group and at least one tertiary amino group, for example, triethanolamine.

The basic catalyst may also be a surface or body to which basic groups are bonded.

In case that the transfer of the hydroxy groups into alcoholate groups is performed in a separate step, the same catalysts may be used.

Catalysts that do not correspond to compound B) itself may be used, for example, in amounts of 0.01 to 1 mol per 1 mol of compound A), preferably in amounts of 0.02 to 0.2 mol per 1 mol of compound A).

If desired, the —SH groups of the obtained compound may be further reacted with a compound C). Any reference to a compound C) shall include a mixture of different compounds C), if not stated otherwise or obvious from the context.

The —SH group is highly reactive and readily reacts with the reactive groups of compound C) that are listed above.

The reaction with compound C) may also be performed in the presence of a catalyst. In case of compounds C) with epoxy groups a basic catalyst such as a tertiary amine, for example Versamin® is preferred, which is the same catalyst that already supports the reaction of compound A) and B). A basic catalyst may also be suitable for compounds C) with non-aromatic, ethylenically unsaturated groups that react via an ionic mechanism. In case of compounds C) with non-aromatic, ethylenically unsaturated groups that react via a radical mechanism, the addition reaction to the —SH group may be catalytically supported by initiators that form radicals. Such initiators are either thermal, redox, electrochemical or photoactive initiators well known from radical polymerization.

The —SH group of the adduct of compound A) and B) may oxidize and form disulfide bridges. Such oxidation may occur notably at room temperature in the presence of oxygen.

Redox stabilizers that reduce or avoid oxidation of S—H groups may be added to the reaction mixture, if desired. An example of such stabilizer is tris(2-carboxyethyl)phosphine (TCEP).

In case that the formation of disulfide bridges is intended, such formation may be supported by the presence of an oxidant or oxidation catalysts which facilitate the rapid formation of disulfides.

The product of compounds A) and B) and optionally C) typically comprises structural elements of formula (IV)

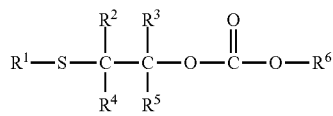

The variables $R^1$ to $R^6$ represent substitutions by any substituents.

The typical structural element is a non-cyclic carbonate group with a sulfur atom being bonded via an ethylene group to the oxygen of the carbonate group.

The reaction of compounds A), B) and C) may be performed in one step or in two steps.

In a one-step reaction all compounds A), B) and optionally C) are reacted simultaneously.

In a two-step reaction, the cyclic monothiocarbonate groups undergo the ring opening reactions with the hydroxy groups in a first step, followed by the reaction of the —SH groups of the obtained intermediate with the reactive groups of compound C).

The one step reaction of compounds A), B) and C) or the second step of the two-step reaction may be performed in the same temperature range and in the presence of the same solvents as described above for the reaction of compounds A) and B).

Preferably, 0.8 to 1.2 mol hydroxy groups of compound B) per 1 mol of five-membered cyclic monothiocarbonate groups of compound A) are reacted, regardless whether the reaction of compounds A), B) and optionally C) is performed in one step or two steps.

To the Polymers Obtained

The polymers comprise repetitive units of non-cyclic carbonates and can be referred to as polycarbonates.

In a preferred embodiment, compound A), compound B) and optionally a compound C) are reacted to obtain a polymeric compound with non-cyclic carbonate groups.

The composition of the polymers obtained depends from the presence or absence of compounds C), the functionality of compounds A), B) and C) and from the process which may be a one-step or two-step process. In case of a one step process a functional group may have competing reaction partners.

In one preferred embodiment, a compound A) comprising at least one five-membered cyclic monothiocarbonate group and at least one non-aromatic, ethylenically unsaturated group or at least one epoxy group is reacted with a compound B) and optionally a compound C).

In this case, the five-membered cyclic monothiocarbonate group is opened with the hydroxy group of compound B) which results in a compound having at least one non-aromatic, ethylenically unsaturated group or at least one epoxy group and, in addition, at least one thiol group. Such a compound may polymerize in form of a head-to-tail polymerization with itself. A further compound C) may be used in this reaction but is not required to have a polymer as result. A compound B) with one hydroxy group would be sufficient.

Preferably, compound A) used in this embodiment, is a compound A) comprising one five-membered cyclic monothiocarbonate group and one non-aromatic, ethylenically unsaturated group or one epoxy group, more preferred is a compound A) comprising one five-membered cyclic monothiocarbonate group and one non-aromatic, ethylenically unsaturated group. The non-aromatic, ethylenically unsaturated group of compound A) is preferably an acrylic or methacrylic group.

Preferably, compound B) used in this embodiment is a compound B) comprising 1 to 5 hydroxy groups, notably 1 to 3 hydroxy groups. In a most preferred embodiment, compound B) does further comprise a tertiary amino group. Such tertiary amino group catalyzes the ring opening.

In a further embodiment,
a compound A1) comprising one five-membered cyclic monothiocarbonate group,
a compound B2) comprising at least two hydroxy groups and
a compound C2) comprising at least two functional groups that react with a thiol group are reacted.

In this embodiment, compound B2) opens the five-membered cyclic monothiocarbonate group of two compounds A1), resulting in an adduct with two thiol groups —SH. The adduct with two thiol groups —SH and compound C2) having at least two groups that react with a thiol group will then polymerize.

In a further embodiment,
a compound A2) comprising at least two five-membered cyclic monothiocarbonate groups,
a compound B) comprising at least one hydroxy group and
a compound C2) comprising at least two functional groups that react with a thiol group are reacted.

In this embodiment, the at least one hydroxy group of compound B) opens the five-membered cyclic monothiocarbonate groups of compound A2), resulting in an adduct with at least two thiol groups —SH. The adduct with at least two thiol groups —SH and compound C2) having at least two groups that react with a thiol group will then polymerize.

In a further embodiment,
a compound A2) comprising at least two five-membered cyclic monothiocarbonate groups,
a compound B2) comprising at least two hydroxy groups and
optionally a compound C) comprising at least one functional group that react with a thiol group are reacted.

In this embodiment, the at least two hydroxy groups of compound B2) open the at least two five-membered cyclic monothiocarbonate groups of compound A2), resulting in an adduct with at least two thiol groups —SH. This is already a polymerization reaction, and the adduct obtained is a polymer comprising thiol groups —SH. The thiol groups —SH may be further reacted with a compound C). A compound C) with one thiol group results in a polymer which is substituted by thioether groups, a compound C) with at least two reactive groups results in crosslinking of the polymer.

In one embodiment of the invention, compound A) comprises at least one five-membered cyclic monothiocarbonate group and at least one hydroxy group.

Compounds A) comprising one five-membered cyclic monothiocarbonate group and one hydroxy group can undergo a head-to-tail polymerization with themselves resulting in a linear polycarbonate with thiol groups.

Compounds A) comprising more than one five-membered cyclic monothiocarbonate group and optionally more than one hydroxy group can undergo a head-to-tail polymerization with themselves resulting in a branched or crosslinked polycarbonate with thiol groups.

In a preferred embodiment, compounds A) comprising at least one five-membered cyclic monothiocarbonate group and at least one hydroxy group are polymers. Such polymers could be obtained, for example, by copolymerization of 5-(methacryloyloxy)methyl-1,3-oxathiolane-2-one or 5-(acryloyloxy)methyl-1,3-oxathiolane-2-one with hydroxy group comprising monomers, such as hydroxy alkyl(meth)acrylates. The resulting polymeric compound A) is easily cross-linkable by reacting the monothiocarbonate groups with the hydroxy groups.

Further reactive compounds may be used in the synthesis of the above polymer. For example, compounds D) with primary or secondary amino groups may be used. These compounds react with compounds A) in a similar ring opening reaction to a compound comprising urethane groups, as described in WO 2019/034470 A1 or WO 2019/034473 A1. By using mixtures of compounds B) and D) a polymeric compound with non-cyclic carbonate groups and urethane groups may be obtained. Suitable are also compounds D) which comprise primary or secondary amino groups and, in addition, hydroxy groups. As the amino groups have higher reactivity than the hydroxy groups, the amino groups react first with the cyclic monothiocarbonate.

In a preferred embodiment, the polymer obtained consists to at least 40% by weight, more preferably to at least 60% by weight, most preferably to at least 80% by weight of compounds A), B) and C), only. In a specifically preferred embodiment, the polymer obtained consists to at least 95% by weight of compounds A), B) and C). Notably, the polymer obtained consists to 100% by weight of compounds A), B) and C).

Additives, such as stabilizers, preservatives, biocides or additives that are required in the application of the polymer obtained, for example, in the field of adhesives, sealants or coatings may be already added before or during the reaction or may be added afterwards.

The obtained polymers are usually transparent, non-tacky and solid at room temperature.

The process of this invention provides an alternative method for the manufacturing of polymers with carbonate groups. The process of this invention is an easy and effective manufacturing process, notably a process not requiring high energy or high temperatures. Solid and transparent polymers are easily available and are useful for a variety of technical applications such as coatings, adhesives, thermoplastic or duroplastic material for the formation of molds in any form.

Hybrid polymers comprising carbonate groups and other functional groups are available. Optical polymers with high refractive index are accessible. Polymers obtained show high thermal stability. The process furthermore offers a curing mechanism for low temperature curing which is compatible with the presence of oxygen.

The process also provides an alternative synthesis to manufacturing non-cyclic carbonates, for example, a compound of formula (IIIa). Compound of formula (IIIa) provides the advantage of offering high cross-link density under curing conditions.

EXAMPLES

Example 1

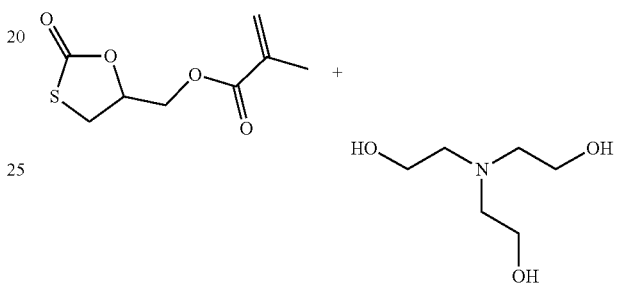

A 10 ml flask was charged with 4.0 g of 2-propenoic acid, 2-methyl-(2-oxo-1,3-oxathiolane-5-yl)methyl ester (5-(methacryloyloxy)methyl-1,3-oxathiolane-2-one) (MMA-TC). The temperature was increased to 50° C. To the melt 1.0 g of triethanolamine was added, and the mixture was stirred thoroughly and subsequently kept at 40° C. for 24 hours.

The resulting polycarbonate polymer was isolated as a white and hard solid material showing some polymer foam characteristics.

Shore D hardness: 20 (measured with digital durometer for Shore D hardness testing by BAQ, corresponding to DIN 53505 and ASTM D 2240)

Example 2

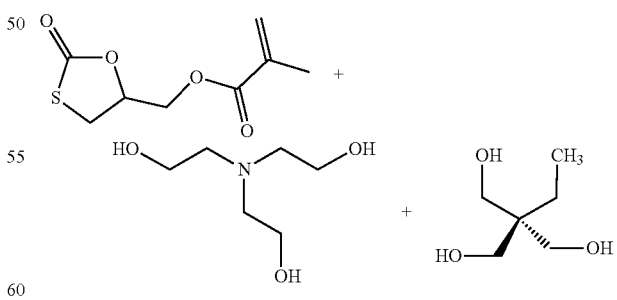

A 10 ml flask was charged with 0.25 g of triethanolamine and 0.66 g of 1,1,1-trimethylpropane (TMP). Under stirring 4.0 g of 2-propenoic acid, 2-methyl-(2-oxo-1,3-oxathiolane-5-yl)methyl ester (MMA-TC) were added. The temperature was increased to 50° C. until a homogeneous mixture was obtained. The mixture was kept at 50° C. for curing. After 3 hours the mixture turned into a solid rubber-like polymer. After 72 hours at 50° C. a solid polymeric polycarbonate was obtained.

Example 3: Synthesis of a Bisthiocarbonate a) Preparation of a Bis-Thiocarbonate from Bisglycidyl Carbonate
a1) Preparation of Bisglycidyl Carbonate

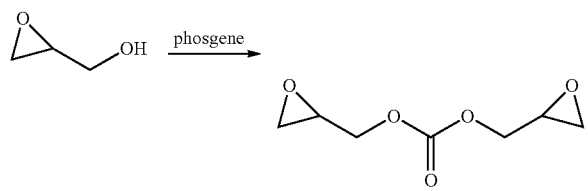

In a 2 L stirring apparatus equipped with two condensers (−30° C. and −78° C. (dry ice)) phosgene dip pipe and internal thermometer 74.1 g (1.0 mol, 1.00 eq.) glycidol and 106.3 g (1.05 mol, 1.05 eq.) triethylamine were dissolved in 500 ml of toluene under an atmosphere of nitrogen. After the addition of the starting materials the reaction mixture was cooled to 10° C. After the mixture reached this temperature gaseous phosgene (overall 55.0 g, 0.56 mol, 0.56 eq.) was added to the reaction mixture via the dip pipe. The temperature of the reaction mixture was continuously monitored and was kept at 10° C. by carefully adjusting the rate of the phosgene addition. After the phosgene addition was completed the initial cooling of the reaction mixture was removed, and the reaction mixture was allowed to warm up to room temperature (ca. 25° C.). The colorless suspension was stirred at room temperature for a further hour, before it was stripped, with nitrogen at room temperature, phosgene-free. Afterwards the precipitated triethylammonium chloride was filtered off, and the filtrate was extracted two times with a saturated potassium carbonate solution. The organic phase was dried over $Na_2SO_4$, and afterwards all volatiles were removed under reduced pressure. The resulting pale brown, viscous oil (79.1 g, 0.45 mol, >90% yield, mixture of diastereomers: 1:1) was directly used, without further purification, for the thiocarbonate formation.

a2) Phosgenation of Bisglycidyl Carbonate

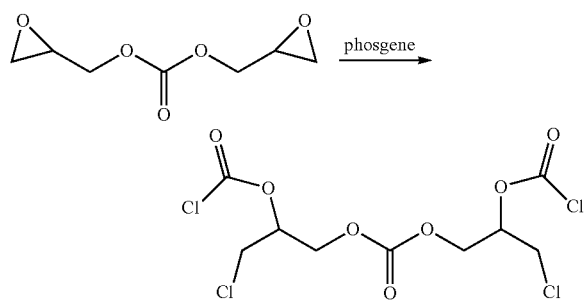

Into a 0.25 L stirred tank glass reactor equipped with two condensers (−30° C. and −78° C. (dry ice)) phosgene dip pipe and internal thermometer 305 g (1.75 mol, 1.00 eq.) of bisglycidyl carbonate were introduced under an atmosphere of nitrogen. After the addition of the starting material the cooling of the tank reactor was turned on and was adjusted to 10° C. After the reactor reached this temperature, 4.86 g (0.0170 mol, 1.00 mol %) of tetrabutylammonium chloride (TBACl) were suspended in the starting material. Afterwards phosgene (overall 408 g, 4.16 mol, 2.36 eq.) was added to the reactor via the dip pipe. The temperature of the reaction mixture was continuously monitored and was kept below 25° C. by carefully adjusting the rate of the phosgene addition. Overall the phosgene addition took approximately 6 hours. After the phosgene addition was completed the initial cooling of the reactor was turned off, and the reactor was allowed to slowly reach room temperature (ca. 25° C.). Afterwards the reaction mixture was stirred at room temperature for 2 hours. Finally, the reaction mixture was stripped, with nitrogen at room temperature, phosgene-free overnight. The resulting pale brownish, highly viscous oil (599 g, 1.61 mol, 92% yield, regioisomeric purity: >95%) was directly used, without further purification, for the thiocarbonate formation.

b) Synthesis of bis[(2-oxo-1,3-oxathiolane-5-yl)methyl] carbonate (carbonate-dithiocarbonate)

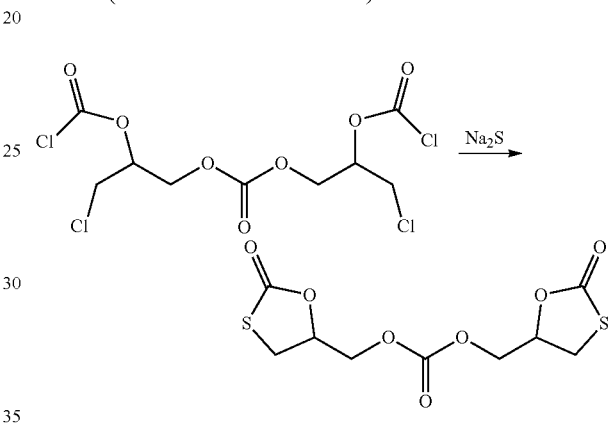

The respective β-chloroalkyl chloroformiate (bis(3-chloro-2-chlorocarbonyloxy-propyl) carbonate) (650 g, 1.75 mol) and dichloromethane (2.5 L) were placed in a 7 L reactor. The solution was cooled down to 0° C. before $Na_2S$ (2 eq., 15 wt % aqueous solution) was slowly added, maintaining the temperature at 5° C. After the complete addition the reaction mixture was allowed to warm to room temperature. The phases were separated, and the aqueous phase was extracted with dichloromethane (0.5 L). The solvent was removed from the combined organic phases under reduced pressure. The obtained yellow solid was washed with warm methanol (3×0.5 L), the resulting off-white solid was dried under vacuo (300 g, 58%). Melting point: 108-115° C.

1H NMR (400 MHz, CDCl3): δ [ppm] 3.4-3.7 (4H, C$\underline{H}_2$O), 4.4-4.55 (4H, SC$\underline{H}_2$), 4.9-5.0 (2H, C$\underline{H}$O)

Onset temperature (DSC, glass): 240° C. (determined by differential scanning calorimetry (DSC) in a temperature range of 30 to 410° C. at a heating rate of 2.5 K/min (after 10 min at 30° C.) in air atmosphere)

The invention claimed is:
1. A process for the synthesis of a compound comprising at least one non-cyclic carbonate group, the process comprising:
    transferring at least one hydroxy group of a compound (B) or of a compound (A) into at least one alcoholate group,
    reacting the compound (A) comprising at least one five-membered cyclic monothiocarbonate group with at least one alcoholate group of compound (B) or of compound (A) itself;

wherein the at least one hydroxy group of compound (B) or of compound (A) is transferred into the at least one alcoholate group before the reacting or by a catalyst used in the reacting.

2. The process according to claim 1, wherein compound (A) is a monothiocarbonate of formula (I)

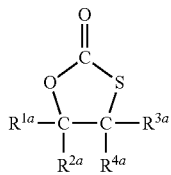

(I)

with $R^{1a}$ to $R^{4a}$ independently from each other representing hydrogen or an organic group with up to 50 carbon atoms, whereby, alternatively, $R^{2a}$, $R^{4a}$ and two carbon atoms of the thiocarbonate group together form a five to ten membered carbon ring.

3. The process according to claim 1, wherein compound (A) is a compound of formula (II)

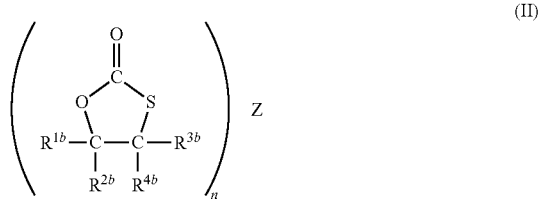

(II)

with $R^{1b}$ to $R^{4b}$ independently from each other representing hydrogen or an organic group with up to 50 carbon atoms, whereby, alternatively, $R^{2b}$, $R^{4b}$ and two carbon atoms of the thiocarbonate group together form a five to ten membered carbon ring, and wherein one of the groups $R^{1b}$ to $R^{4b}$ is a linking group to Z, n represents an integral number of at least 2, and Z represents a n-valent organic group.

4. The process according to claim 1, wherein compound (A) and compound (B) are reacted in presence of a compound with a tertiary amino group.

5. The process according to claim 1, wherein compound (B) comprises a tertiary amino group.

6. The process according to claim 1, wherein compound (A) and compound (B) are reacted optionally, with a compound (C) comprising at least one functional group that reacts with a thiol group —SH, to obtain a polymeric compound with non-cyclic carbonate groups.

7. The process according to claim 6, wherein compound (A) comprises the at least one five-membered cyclic monothiocarbonate group and at least one non-aromatic, ethylenically unsaturated group or at least one epoxy group; and compound (B) comprises the at least one hydroxy group.

8. The process according to claim 7, wherein the at least one non-aromatic, ethylenically unsaturated group is an acrylic group or a methacrylic group.

9. The process according to claim 6, wherein
compound (A) is a compound (A1) comprising one five-membered cyclic monothiocarbonate group,
compound (B) is a compound (B2) comprising at least two hydroxy groups, and
compound (C) is a compound (C2) comprising at least two functional groups that react with a thiol group.

10. The process according to claim 6, wherein
compound (A) is a compound (A2) comprising at least two five-membered cyclic monothiocarbonate groups,
compound (B) comprises the at least one hydroxy group, and
compound (C) is a compound (C2) comprising at least two functional groups that react with a thiol group.

11. The process according to claim 6, wherein
compound (A) is a compound (A2) comprising at least two five-membered cyclic monothiocarbonate groups, and
compound (B) is a compound (B2) comprising at least two hydroxy groups.

12. The process according to claim 6, wherein compound (B) is used in combination with a compound comprising at least one amino group selected from the group consisting of primary amino groups and secondary amino groups, to obtain a polymeric compound with non-cyclic carbonate groups and urethane groups.

13. A polymer obtainable by the process according to claim 6.

14. The process according to claim 1, wherein compound (A) is a polymer comprising the at least one five-membered cyclic monothiocarbonate group and the at least one hydroxy group.

15. A polymer obtainable by the process according to claim 14.

16. A carbonate compound of formula (IIIa)

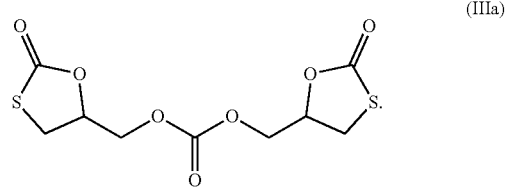 [SMILES: O=C(OCC1CSC(=O)O1)OCC1CSC(=O)O1]

(IIIa)

* * * * *